United States Patent [19]

Bekey et al.

[11] 4,445,854
[45] May 1, 1984

[54] APPARATUS FOR CONSTRUCTING REGISTERED TEETH CASTINGS

[76] Inventors: Ivan Bekey, 4624 Quarter Charge Dr., Annandale, Va. 22003; Roger S. Wolk, 23716 Malibu Colony Dr., Malibu, Calif. 90265

[21] Appl. No.: 362,426

[22] Filed: Nov. 19, 1981

Related U.S. Application Data

[60] Continuation of Ser. No. 166,435, Jul. 7, 1980, abandoned, which is a continuation-in-part of Ser. No. 960,381, Nov. 13, 1978, abandoned, which is a division of Ser. No. 745,712, Nov. 29, 1976, Pat. No. 4,161,067.

[51] Int. Cl.³ .............................................. A61C 9/00
[52] U.S. Cl. ........................................ 433/37; 433/42
[58] Field of Search ..................... 433/37, 38, 41, 42, 433/71

[56] References Cited

U.S. PATENT DOCUMENTS

| | | | |
|---|---|---|---|
| 347,976 | 8/1886 | Starr | 433/41 |
| 522,212 | 7/1894 | How | 433/42 |
| 696,774 | 4/1902 | Tiffin et al. | 433/42 |
| 730,658 | 6/1903 | Huber | 433/42 |
| 1,385,505 | 7/1921 | Supplee | 433/48 |
| 1,486,039 | 3/1924 | Santos | 433/43 |
| 2,053,914 | 9/1936 | Mann | 433/48 |
| 2,428,773 | 10/1947 | Beresin et al. | 433/36 |
| 2,564,167 | 8/1951 | McLaughlin | 433/48 |
| 2,594,832 | 4/1952 | Wentzel | 433/41 |
| 2,713,202 | 7/1955 | Jones | 433/41 |
| 3,250,004 | 5/1966 | Jones | 433/38 |

FOREIGN PATENT DOCUMENTS

824673 7/1949 Fed. Rep. of Germany ........ 433/37

*Primary Examiner*—John J. Wilson
*Attorney, Agent, or Firm*—Nilsson, Robbins, Dalgarn, Berliner, Carson & Wurst

[57] ABSTRACT

A system and method is disclosed for obtaining precisely registered, articulated castings of upper and lower dental impressions. The dental impressions are obtained through use of a dental tray. The tray has an upper and a lower section, each having a non-porous, bite-deformable central septum. Each tray section has a U-shaped peripheral wall. The tray sections are placed back-to-back so that the septums are in movable contact with each other. Means are provided to maintain the upper and lower tray sections in position with respect to each other once they have been adjusted. A cavity is formed in the upper or lower tray section, or both, adjacent to the anterior portion of the peripheral retaining wall. The cavity extends past the dividing septums to accommodate gross overbite and/or underbite conditions.

1 Claim, 18 Drawing Figures

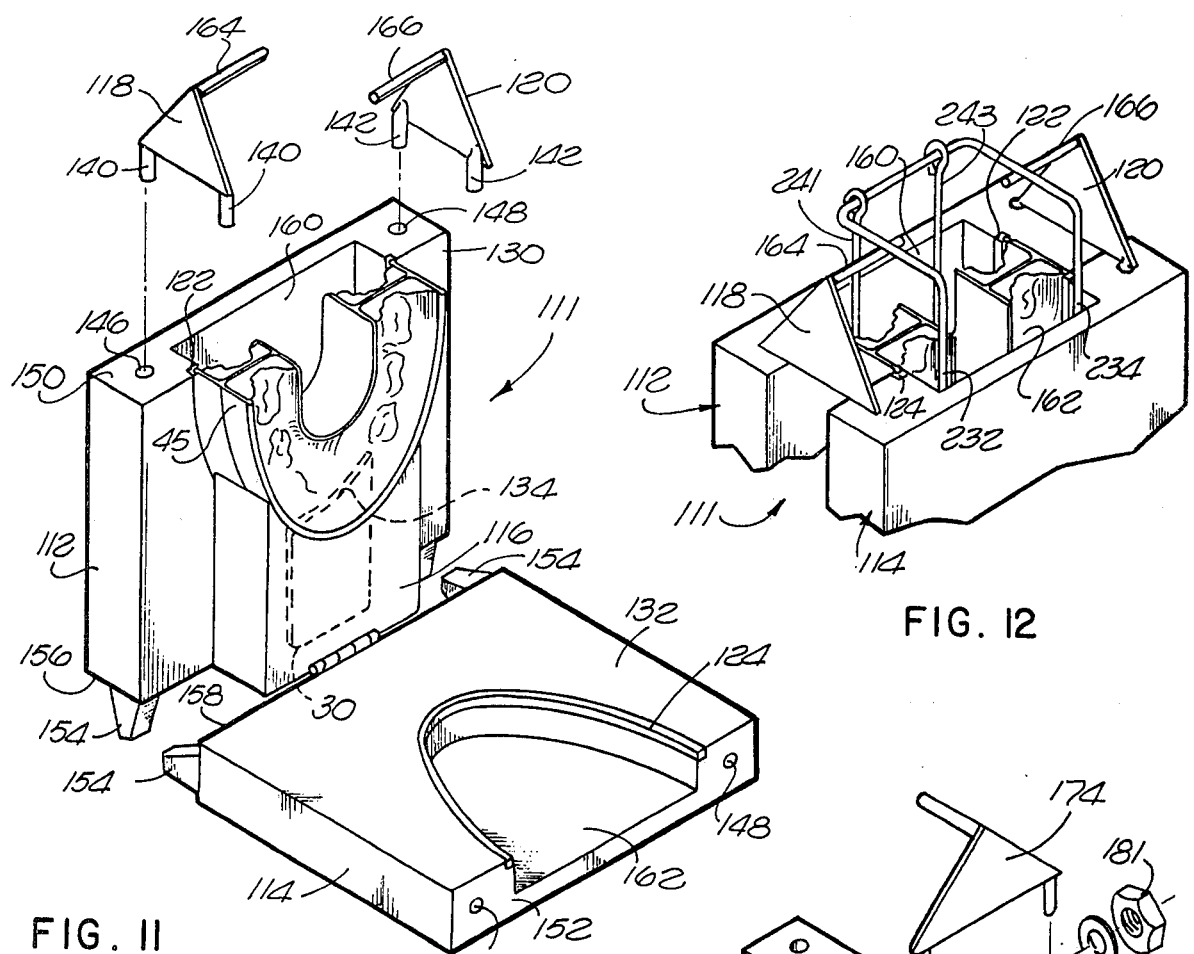
FIG. 11
FIG. 12
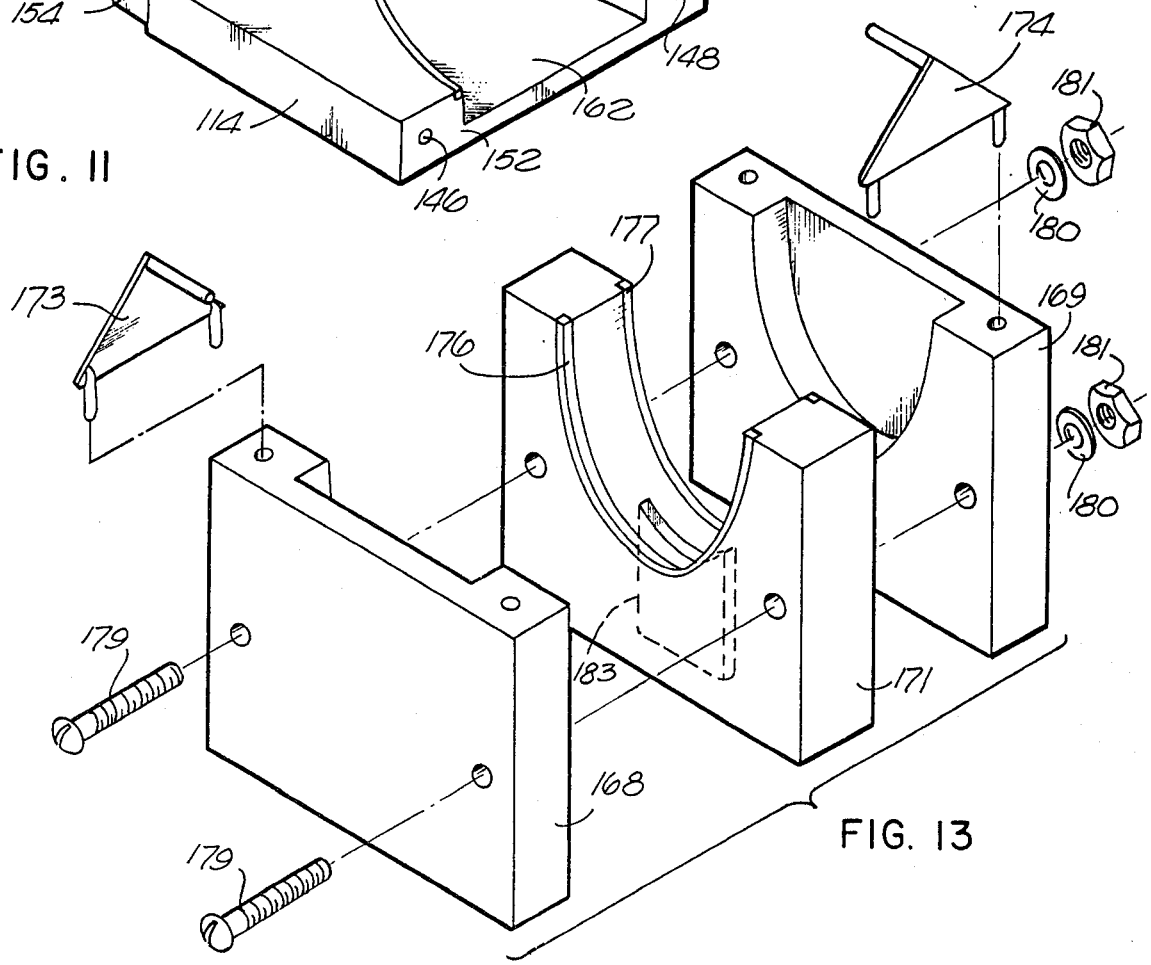
FIG. 13

4,445,854

APPARATUS FOR CONSTRUCTING REGISTERED TEETH CASTINGS

This is a continuation, of Application Ser. No. 166,435, filed July 7, 1980, now abandoned, which was a continuation-in-part of U.S. Ser. No. 960,381 filed Nov. 13, 1978, now abandoned, which was a division of U.S. Ser. No. 745,712 filed Nov. 29, 1976, now issued as U.S. Pat. No. 4,161,067.

BACKGROUND OF THE INVENTION

This invention relates to apparatus and methods for taking dental impressions and, more specifically, for taking registered impressions of upper and lower teeth in full occlusion and converting these impressions into castings which are used for analysis by the dentist, displays for patient consultations, laboratory work, and, when properly mounted and registered, for correct bite registration. Present methods for preparing these castings require taking upper and lower impressions with separate sequentially applied trays filled with an impression material. Upon hardening, a separate plaster casting is poured for each tray. It is often desirable to register the castings so that they fit together in the same manner as if in the patient's mouth. This has previously been accomplished by placing a relatively thin sheet of wax between the teeth and having the patient bite into the wax to form simultaneous indentations in the wax of both the upper and lower cusp tips of the teeth as they fit together. This wax bite impression is then employed to register the upper and lower dental casts in their proper occlusion. With the wax bite in place between the teeth castings, the castings are trimmed on their posterior faces as well as other surfaces to form artistic occlusally registered models. An articulator may also be attached to the castings to allow them to hinge. This procedure entails a large amount of time, labor, cost, sometimes patient discomfort, and has many opportunities for inaccuracy of registration, all of which are greatly reduced by the system disclosed herein.

SUMMARY OF THE INVENTION

A system is provided for constructing registered castings of precisely registered upper and lower dental impressions. The system includes a novel dental tray including a U-shaped peripheral retaining wall. The tray is divided into an upper and lower portion by a non-porous, bite-deformable septum attached to the retaining wall. The two portions are adapted to hold impression material so that as the patient bites, both upper and lower dental impressions are simultaneously obtained. These impressions are obtained within the mouth.

In addition, dental trays are provided which can accommodate an overjet condition wherein the upper teeth extend forward horizontally with respect to the lower teeth, a negative overjet condition wherein the lower teeth extend forward horizontally with respect to the upper teeth, an overbite condition wherein the upper front teeth overlap vertically the lower front teeth, and an openbite condition wherein the lower front teeth do not fully close in a vertical plane to the upper front teeth.

BRIEF DESCRIPTION OF THE DRAWINGS

In the drawings which consitutue a part of this specification, exemplary embodiments demonstrating various features of this invention is set forth wherein:

FIG. 11 is a perspective view of the mold of this invention with one of the end pieces rotated outward to show positioning of the dental tray within the dental tray support;

FIG. 12 is a perspective view of the top of the mold showing the dental tray held by the mold and an articulator supported in position;

FIG. 13 is an exploded, perspective view of a second embodiment of the mold of this invention which can be adapted to hold dental trays of varying peripheral contours;

DESCRIPTION OF THE INVENTION

Figure 1:
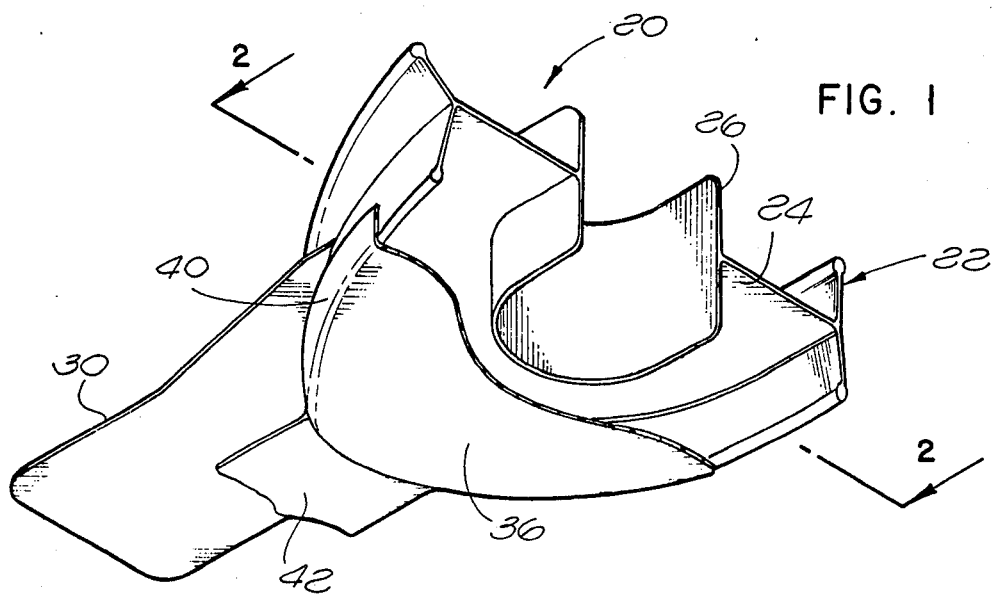
FIG. 1 is a perspective view of the first embodiment of the dental tray of this invention.

The system disclosed herein provides a means for obtaining registered castings of upper and lower dental impressions in a one-step technique. The basic elements which comprise the system consist of a dental tray 20, dental tray bottom cover 36, and a mold 111 for which the castings are made. When articulated castings are desired, the system includes an articulator 220.

The dental impression tray 20 not only takes registered impressions of the biting surfaces of the teeth, but also provides for an accurate impression of all the soft tissue and bony structures of the mouth. The dentist is not only interested in the biting surfaces but also must study tooth form, bony contours and soft tissue and ligamentous attachments. Therefore, tray side walls 22 must be of sufficient vertical height to provide for impressions of these structures. While the impression tray must have adequate vertical height, it must still be small enough to fit into the patient's mouth.

The dental tray 20 is divided into an upper and lower portion by a bite-deformable septum 24. A center support 26 is provided for containing the impression material and providing tongue relief. When dental impression material is placed in the upper and lower portions of the dental tray 20 and the tray is inserted into the mouth, the patient by biting down simultaneously creates registered impressions of the upper and lower teeth, gums and bony anatomy in the impression material. The bit-deformable septum 24 allows the cusp tips of the upper and lower teeth to interdigitate in full occlusion. The bottom cover 36 is used to prevent flow of the dental impression material out of the lower portion of the tray during insertion of the dental tray 20 into the patient's mouth, and is removed subsequent to insertion. The registration of these impressions carries through to the final casting.

The dental tray 20 is removed from the patient's mouth and is placed in a mold 111 which is adapted to create two mold cavities, each of which is partially lined by one of the dental impressions. This is accomplished by placing the dental tray 20 in dental tray support 116 so that the U-shaped portion of the dental tray 20 is supported by the U-shaped portion of the tray support 116. End pieces 112 and 114, which are rotatably attached to the bottom of the tray support 116, are rotated inwardly until a seal is formed with the rim of dental tray 20. This seal is maintained by clamping end pieces 114 and 116 together with articulator supports 118 and 120. In an alternative sealing method or when varying shaped dental trays are utilized, end pieces 168 and 169 are clamped to dental tray support 171 which in turn supports the U-shaped portion of the dental tray. Any spaces between the U-shaped portion of the dental tray and the dental tray support 171 are filled with a suitable sealant material.

When articulation is desired, articulator 220 is suspended from the support extensions 164 and 166 so that the first articulator support structure 224 partially extends into one mold cavity and the second articulator support structure 226 extends into the second mold cavity. With the articulator 220 thus supported, casting material is poured into each of the two cavities. After the casting material has set, end pieces 114 and 116 are rotated outwardly and articulated castings of registered upper and lower dental impressions removed.

THE DENTAL TRAY

The dental tray 20 shown in FIG. 1 consists of a U-shaped peripheral retaining wall 22, a bite-deformable septum 24, a center support 26 for tongue relief and palatal roof for containment of the impression material, and a handle 30. The U-shaped wall 22 and center support 26 may be constructed of molded plastic or a deformable material, such as rigidized foam, which may be adjusted to the shape of the mouth during insertion. The handle 30 is made of a similar plastic material and can be either integral or attached with a suitable adhesive. The bit-deformable septum 24 is composed of a thin layer of non-porous, bite-deformable plastic or metal, such as tin, zinc lead, aluminum or their alloys such as commonly used in toothpaste tubes. The term "bite-deformable" or "deformable" is used herein to describe a material which is very thin but semirigid, and must also be able to be deformed when bitten into to allow all upper or lower teeth to come into full occlusion. If the material is either too thick or too rigid, the back (posterior) teeth will not be able to close enough to allow the front teeth to come together. One must bear in mind that the lower jaw hinges in an arc-like and closes toward the upper jaw with a wedge effect. For example, during opening, when the molars ar one millimeter apart the insisors are two to three milimeters apart. Thus, it is clear to see that the molars must be fully closed in order for the front teeth to reach occlusion.

This septum must allow deformation during occlusion (like wax or chewing gum) but must not break or perforate. This way the upper and lower impressions are kept separate and apart from each other, but the septum's deformability allows bite registration. After the impression is taken, the septum must remain rigid enough to ensure dimensional accuracy of the impression material. If any of the surfaces of the tray are too flexible, the impression material cannot maintain its dimensional accuracy.

The bite-deformable septum 24 is attached by adhesive or the like or formed integrally along a median line 32 so that the U-shaped wall 22 is divided into substantially equal upper and lower portions which will contain the impression material for the upper and lower dental impressions. The adhesive at the anterior portion of the septum may be weakened, or the septum may be perforated adjacent the connecting point between the retaining wall 22 and the anterior portion of the septum. In this manner, pressure exerted by a patient's teeth will cause the septum to conform to the contours of the biting surfaces without tearing or perforating. It will maintain this deformed relationship but will remain semi-rigid so that the impression material will have three-dimensional support. This insures accuracy of the impression. The non-porous characteristic of the septum 24 insures that impressions made by teeth biting together will not allow castings to be joined together during the casting procedure. Tears, voids or performations would destructively connect the simultaneous castings of such impressions and prevent separation. The center support 26 is likewise attached to the deformable septum 24 such that it is divided into an upper and lower portion. It is important that the deformable septum 24 be composed of a pliable material that can adjust to and retain the impression of the bite of a set of teeth.

Figure 2:
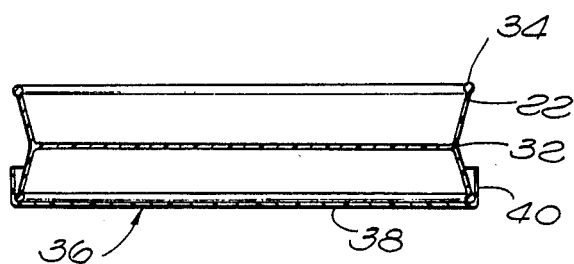
FIG. 2 is a cross-sectional, elevational view taken along line 2—2 of FIG. 1.

As is shown in FIG. 2, the sides of U-shaped wall 22 may be slanted slightly outwardly from median line or seam 32 so that the finished casting can be readily removed. A rounding bead 34 is provided around the upper and lower perimeters of the U-shaped wall 22 to prevent irritation of the gums.

A bottom cover 36, shown in FIGS. 1 and 2, for the dental tray 20 provides support for the impression material during insertion of the tray into the mouth. The upper rim of the tray wall may be provided with a bead similar to the bead 34. The bottom cover 36 is removed after the dental tray 20 has been properly positioned in the mouth. The cover 36 consists of a relative thin base 38, a peripheral side wall 40, and a handle 42. The base 38 and handle 42 may be formed integrally of a single sheet of thin plastic material and the side wall 40 attached to the base 38 by a suitable adhesive, of the entire structure may be integrally formed as a single unit. The contour of side wall 40 must be such that base 38 can be positioned flush with the bottom rim of U-shaped wall 22, thus preventing leakage of the impression material. The side wall 40 need only be high enough to prevent the oover 36 from sliding off the tray further into the mouth during insertion.

Figure 3:
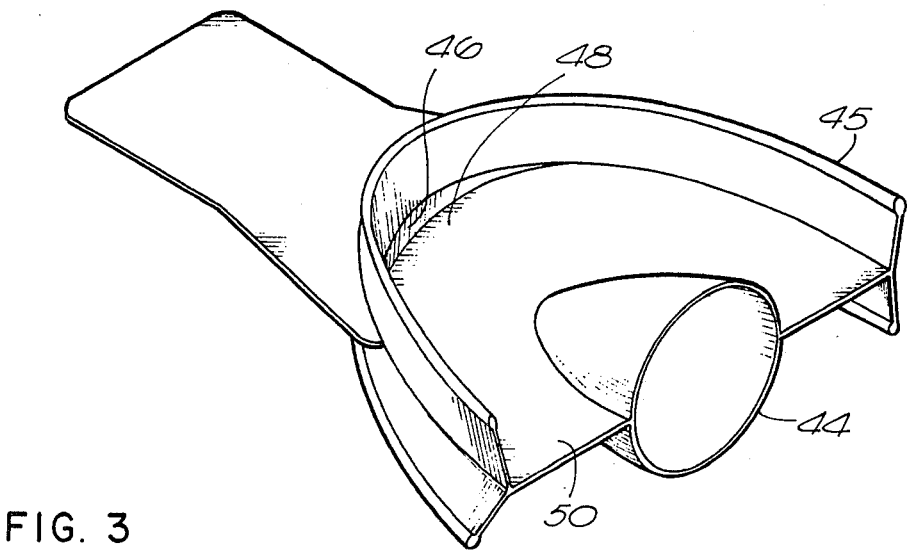
FIG. 3 is a perspective view of a second embodiment of the dental tray of this invention.

In the second embodiment of the dental tray 20, shown in FIG. 3, the tray of FIGS. 1 and 2 is employed with a modified center support 44 consisting of a hollow double convex shaped chamber. This support 44 provides an alternative construction for tongue relief and containment of the impression material to support the palatal part of the impression while eliminating uncomfortable edges abutting against the roof of the mouth. As shown in FIG. 3 but incorporated in both the first and second embodiments, the deformable septum 50 is detached from the U-shaped peripheral retaining wall 45 at the cutout portion 46 to form a movable flap portion 48 of the septum 50. The cutout portion 46 is small enough to insure that both the upper and lower front teeth are covered by the flap. Thus, mild overbites or underbites are accommodated without tearing the septum from the back of the tray in an uncontrolled manner. If the vertical overbite of the front teeth is excessive, the front teeth will bite the front of the septum first, normally preventing the back teeth from closing into full occlusion, or it may cause tearing of the septum from the side walls of the tray. The movable flap on the anterior portion of the tray allows for the back teeth to reach full occlusion without tearing while the front teeth merely push the flap upward or downward. Thus, the patient's impression can be taken without tearing the septum of the impression tray. Alternatively, it is possible that a lesser amount of adhesive or no adhesive at all might be applied to a selected portion of the junction between the U-shaped wall 22 or 45 and the anterior portion of the septum 24 or 50 to provide for an easy break-away flap if the pressure from an underbite or overbite is sufficient to break that portion of the septum away from the wall.

Figure 4:
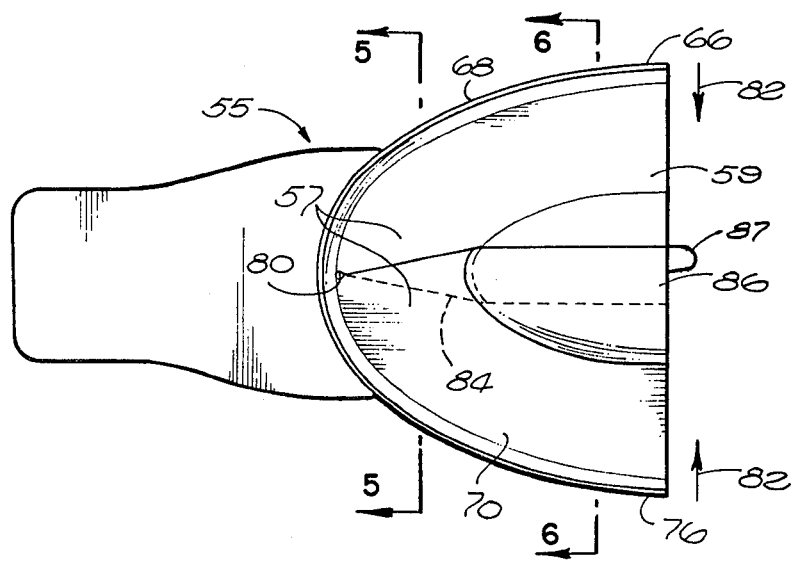
FIG. 4 is a top plan view of a third embodiment of the dental tray of this invention having an adjustable width.
Figure 5:
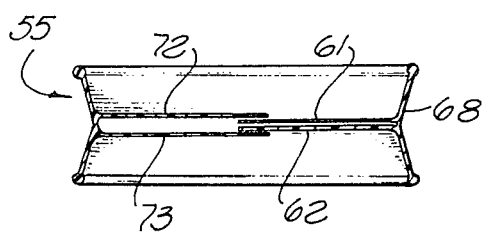
FIG. 5 is a cross-sectional, elevational view taken along line 5—5 of FIG. 4.
Figure 6:
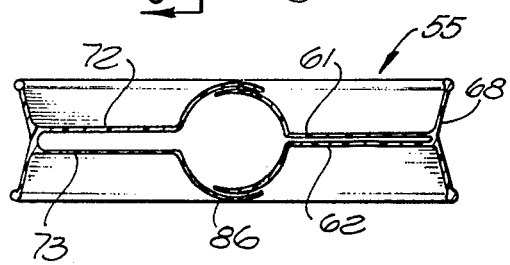
FIG. 6 is a cross-sectional, elevational view taken along line 6—6 of FIG. 4.

In a third embodiment of this invention shown in FIG. 4, the width of the dental tray 55 is made variable by providing a two piece, double layer septum 57. A first septum half 59, consisting of two layers 61 and 62, is attached to the first half 66 of U-shaped wall 68 and a second septum half 70, consisting of two layers 72 and 73, is attached to the second half 76 of wall 68. As is shown in FIGS. 5 and 6, the first septum half 59 slides between the two layers 72 and 73 of the second septum half 70. The wall 68 is made of a flexible or deformable material, such as plastic or metal, to allow the two septum halves 59 and 70 to slide over each other as compressive forces are applied to the wall 68 when the tray is inserted into a small mouth or the like. This enables the two septum halves to, in effect, pivot about the point 80 where the two septum halves join at the wall 68. Thus, as inward pressure is applied to the terminal ends of U-shaped wall 68, as indicated by the arrows 82, the resulting compression results in the first septum half 59 sliding further in between layers 72 and 73 as indicated by dotted line 84 in FIG. 4. Center support 86 is also part of this double layered construction, as is shown in FIGS. 4 and 6, with the center support being mere continuations of the layers 61, 62, 72 and 73. Once the proper width has been established, the layers are held in position with respect to each other by a fastener or a suitable adhesive, or by a deformable tang 87 formed as an extension of the center support 86 on the tray itself, so that they remain fixed after the impression is taken. In addition, the front portion of septum 57 is detached from the front portion of U-shaped wall 68 to accommodate mild overbites or underbites.

Figure 7:
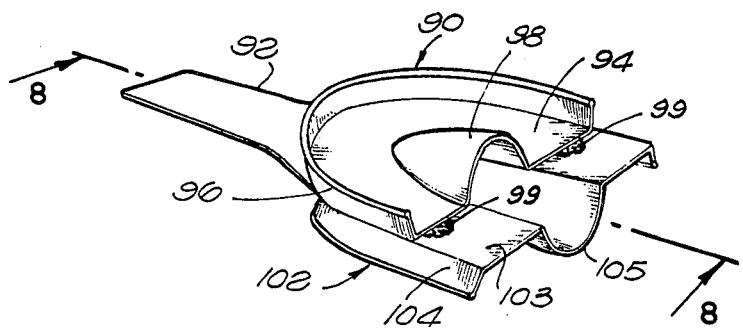
FIG. 7 is a perspective view of a fourth embodiment of the dental tray of this invention which is adjustable to accommodate overbit, underbite, overjet and negative overjet conditions.
Figure 8:
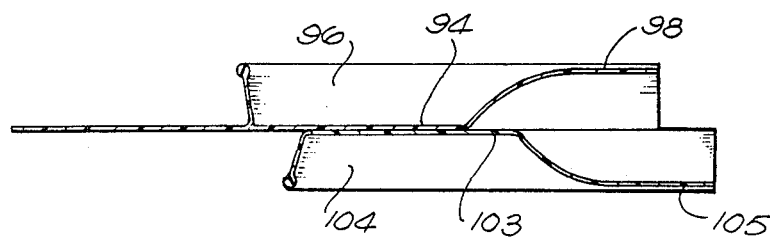
FIG. 8 is a cross-sectional, elevational view taken along line 8—8 of FIG. 7.

The fourth embodiment of the tray of this invention, shown in FIGS. 7 and 8, allows impressions to be made for patients with a gross overbite, underbite, overjet or negative overjet condition. In this embodiment, the tray is bisected horizontally into two portions, the upper portion 90 consisting of a handle 92, deformable septum 94, U-shaped wall 96, and center support 98. Similarly the lower portion 102 consists of a deformable septum 103, U-shaped wall 104, and center support 105. As is shown in FIG. 8, the deformable septums 94 and 103 are attached to the inner rims of U-shaped walls 96 and 104 respectively and to the center supports 98 and 105 respectively. Thus, the upper and lower portions 90 and 102 can be freely positioned with respect to each other, and after the desired offset is obtained to compensate for overbite or overjet, the portions can be attached in the desired position by a fastener, pressure sensitive glue 99, or any adhesive suitable for securing the septums 94 and 103 together. Alternatively the second deformable septum 103 could be eliminated so that the lower portion 102 would be only a shell consisting of the U-shaped wall 104. The center support 105 would be combined with center support 98 forming a single chamber similar to center support 44. In employing such a lower portion 102 without a septum, the lower portion wall 104 would always be positioned against the upper portion septum 94, as is shown in FIGS. 7 and 8, to prevent impression material from flowing from one side of the tray to the other between the walls 96 and 104. In addition, the width adjustment capability described in connection with the third tray embodiment shown in FIGS. 4-6 could be incorporated into this fourth embodiment to produce a tray adaptable to any width mouth and any overbite or underbite condition.

Figure 9:
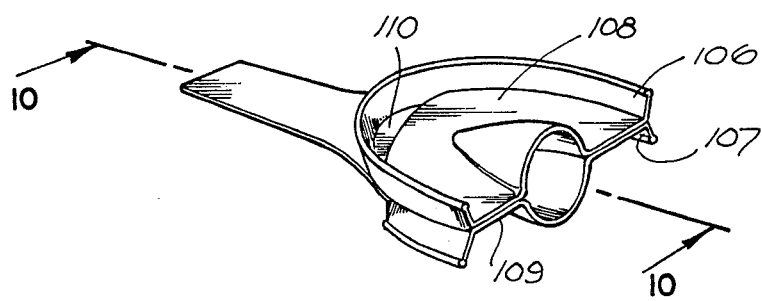
FIG. 9 is a perspective of a fifth embodiment of the dental tray of this invention which will accommodate overbite, underbite, overjet and negative overjet conditions.
Figure 10:
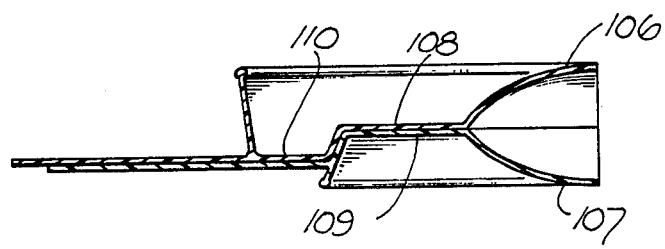
FIG. 10 is a cross-sectional, elevational view taken along line 10—10 of FIG. 9.

A fifth embodiment to accommodate overbite, underbite, overjet and negative overjet conditions is shown in FIGS. 9 and 10. This embodiment consists of two trays 106 and 107, each having a deformable septum 108 and 109, respectively. Cavity 110 is provided to accommodate an overbite or underbite condition. Once the desired offset is obtained, the two trays can be attached by a fastener or any suitable adhesive.

Thus, a dental tray has been described which provides for the simultaneous taking of separate upper and lower dental impression in various mouth widths and accommodating various overbite, underbite, overjet, and negative overjet conditions, all while maintaining these impressions in registration.

THE MOLD

The mold 111 shown in FIGS. 11 and 12 consists of end pieces 112 and 114, dental tray support 116, and articulator supports 118 and 120. The rim of dental tray U-shaped wall 45 abuts against seals 122 and 124, such as a rubber gasket, secured along the inner edges of the flanges 130 and 132 of the end pieces 112 and 114. Alternatively, mold end pieces 112 and 114 could be made of resilient material, thus eliminating the need for seals 122 and 124. The dental tray support 116 has a contoured inner face adapted to receive the bottom portion of the wall of the dental tray. A slot 134 is provided in the support 116 into which handle 30 of the tray is inserted when the dental tray is positioned in the mold. End piece 114 is rotatably mounted to the dental tray support 116 by hinge 136. Similarly end piece 112 is rotatably mounted to the bottom of dental tray support 116 by a hinge which is not shown.

After the dental tray has been inserted into the support structure 116, the end pieces 112 and 114 are rotated inward until seals 122 and 124 are pressed against the upper and lower rims of U-shaped wall 45. Pegs 140 and 142 of the articulator supports 118 and 120 are inserted into holes 146 and 148 in the top walls 150 and 152 of the end pieces 112 and 114, respectively, while the mold is gripping the dental tray. The articulator supports serve to hold the end walls in position as well as to provide articulator support when desired, as will be explained hereinafter. In the above described position, the mold is supported by legs 154 secured to the lower walls 156 and 158 of the end pieces. If the center support 26 of the tray shown in FIG. 1 is utilized, tape or some other isolating material must be placed along its sides to prevent casting material from flowing between the two mold cavities 160 and 162. End pieces 112 and 114, dental tray support 116, and articulator supports 118 and 120 may be made from plastic or any other appropriate material. Support extensions 164 and 166 are provided to hold the articulating structure to be described hereinafter.

Figure 14:
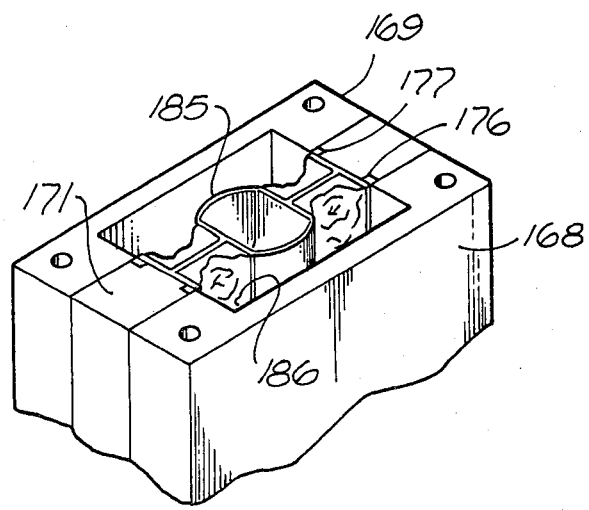
FIG. 14 is a perspective view of the top of the mold of FIG. 13 showing the position of the dental tray within the mold.

The mold shown in FIGS. 13 and 14 is utilized as an alternate sealing method and particularly with an adjustable dental tray, such as those shown in FIGS. 4–10, or with a tray in which the height of the peripheral retaining wall 22 varies. This mold consists of end pieces 168 and 169, dental tray support 171, and articulator supports 173 and 174. Seals 176 and 177 are provided around the inner U-shaped periphery of dental tray support 171. End pieces 168 and 169 are then clamped to each side of dental tray support 171 by bolts 179, washers 180, and nuts 181, or by other suitable clamps or fasteners. In this clamped position seals 176 and 177 abut against end pieces 168 and 169. The bottom portion of the wall of the dental tray rests on the contoured inner face of dental tray support 171 with handle 30 extending into slot 183. Spaces between the dental tray peripheral wall and the dental tray support contoured inner face and between the end pieces 168 and 169 can be filled with soft clay or some other pliant material such that two separate mold cavities 185 and 186 are created.

It will be appreciated that the castings produced by the use of the molds shown in FIGS. 11-14 may be registered by making the top surfaces coplanar. This may be accomplished, for example, by filling the cavities full with casting material and then wiping across the top of the mold with a straight edge. Alternatively, a top plate (not shown) may be provided across the top of the closed mold so that casting material funneled into the mold will rise up to the bottom of the plate and be coplanar across the top of the mold. In this manner, the coplanar surfaces of the castings may be placed on a flat table or the like to automatically register the castings.

THE ARTICULATOR

Figure 15:
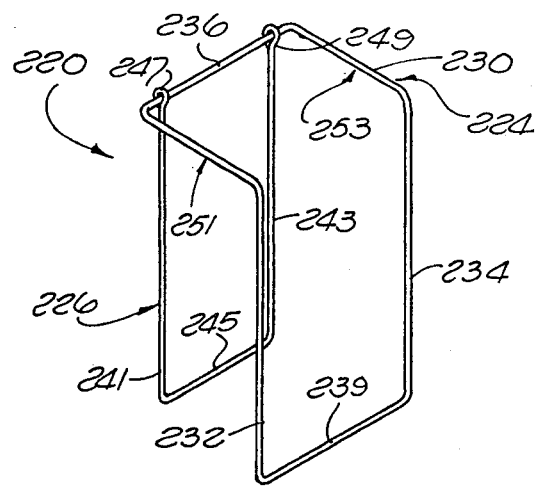
FIG. 15 is a perspective view of the first embodiment of the articulator of this invention.
Figure 16:
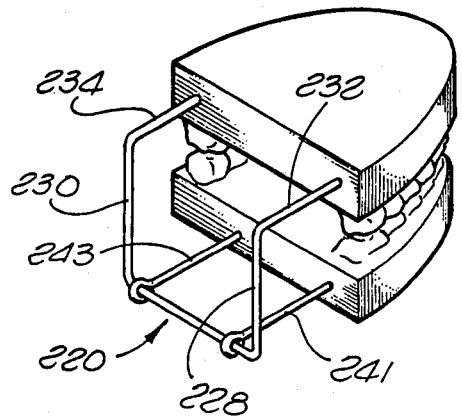
FIG. 16 is a perspective view of articulated registered teeth casting produced with one embodiment of this invention.

The articulator 220 shown in FIG. 15 consists of two support structures 224 and 226, rotatably attached, which are made of a rigid material composed of steel, bronze, aluminum, plastic or the like. The first support structure 224 has two horizontal arms 228 and 230 connecting each of two depending legs 232 and 234. The horizontal arms are connected by a horizontal pivot arm 236 and the depending legs are connected by an end arm 239. The second support structure 226 is U-shaped having two depending legs 241 and 243 connected by an end arm 245. The second support structure depending legs have eyelets 247 and 249 formed respectively at their free ends. The eyelets 247 and 249 encircle the first support structures pivot arm 236 and allow rotation of the two support structures with respect to the other. Alternatively, the articulator could be a one piece plastic structure with a weakened portion forming a hinge. During casting the articulator is supported at points 251 and 253 midway along the horizontal arms 228 and 230 by support extensions 164 and 166, respectively, as shown in FIG. 12. Thus, the end arms and articulator legs extend into the mold so that a predetermined portion of the length of legs 232 and 234 and legs 241 and 243 will be encased by the casting material in opposite mold cavities 162 and 160, respectively, as is shown in FIG. 16.

Figure 17:
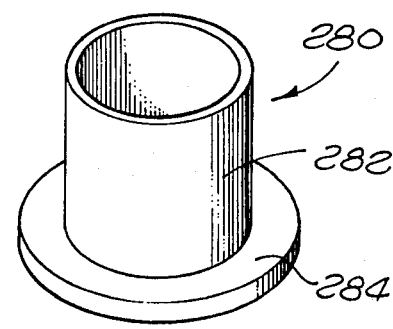
FIG. 17 is a perspective view of an apparatus to be used for attaching each casting to an external articulation device; and, FIG. 18 is a cross-sectional, elevational view of the mold end piece of FIG. 11 showing the apparatus of FIG. 17 mounted in the end piece.
Figure 18:
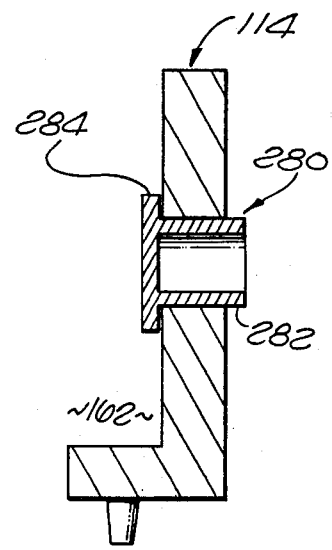

If an external articulator is to be utilized, a flanged, tubular mounting fixture 280, shown in FIG. 17, can be inserted into a circular hole located in the center of mold end pieces 112 and 114, as shown in FIG. 18. The mounting fixture 280 is inserted into each end piece with the cylindrical portion 282 fitted snugly into the end piece and the disk flange portion 284 protruding into mold cavities 160 and 162. After the casting is formed and end pieces 112 and 114 are rotated outward, the mounting fixtures 280 are affixed to the castings by the flanges 284 embedded into the casting material. These mounting fixtures 280 are then used for attachment to external articulation devices and automatically provide for registration of the castings in such articulators. Alternatively, the mounting fixture could be a screw having an enlarged head or a mounting plate embedded into the casting material.

OPERATION

In operation, impression material is placed in one of the dental trays, shown in FIGS. 1, 3, 4, 7, or 10, on both sides of the septum with the lower portion held in place by the bottom cover 36 shown in FIGS. 1 and 2. The tray and bottom cover are inserted in the patient's mouth and the bottom cover removed. The patient then bites down into the impression material and septum to simultaneously form precisely registered impressions of the upper and lower teeth as the impression material sets. After the impression material sats, the tray is removed.

The dental tray is then placed in one of the molds, shown in FIGS. 11 or 13. For the mold of FIG. 11, the mold is closed on the tray to form two sealed cavities 160 and 162 between opposite impressions and the mold end walls. An articulating device, such as is shown in FIG. 15, may be hung from the support extensions 164 and 166 shown in FIG. 12. The casting material is then poured into each mold cavity 160 and 162. When the casting material has hardened, the mold end pieces 112 and 114 are rotated outward, the castings are removed, producing registered, articulated castings of the upper and lower teeth as is shown in FIG. 16. If the mold of FIG. 13 is utilized, an identical process is followed until the casting material has hardened. At that time bolts 179 are removed and end pieces 168 and 169 disengaged from the casting material. The castings are then removed from the dental tray in the form shown in FIG. 16. Alternatively, the castings may merely be registered as previously described.

Thus, the apparatus and method of this invention provides for the simultaneous taking of registered impressions, the simultaneous preparation of registered castings, and articulation of the upper and lower castings without any intermediate steps requiring manual registration or separate handling of the upper and lower impressions or castings. This new and novel method of preparing castings is made possible by utilization of a nonporous, bite-deformable septum in the apparatus described above.

Although detailed embodiments of the system of this invention have been disclosed herein, various other molding techniques and apparatus and modifications of the apparatus disclosed may be utilized in employing this invention, all within the scope of the claims. Consequently, the specific details disclosed herein describe the best presently known embodiments for purposes of disclosure and provide a basis for the claims herein which define the scope of the invention.

What is claimed is:

1. A dental tray for holding impression material, said dental tray being adapted to simultaneously obtain registered upper and lower dental impressions, comprising:

a first U-shaped peripheral retaining wall;

first dividing means, said first dividing means being attached to one of the U-shaped edges of said first wall, said first dividing means and first wall combination comprising an upper tray section;

a second U-shaped peripheral retaining wall;

second dividing means, said second dividing means being attached to one of the U-shaped edges of said second wall, said second dividing means and second wall combination comprising a lower tray section, said upper and lower tray sections being operatively movably placed back-to-back so that said first and second dividing means are in contact with each other, said first and second dividing means being non-porous and deformable when bitten to conform to the contours of the biting surfaces without tearing or perforating while at the same time maintaining the deformed relationship after the biting surfaces are removed, said respective dividing means being thin enough to allow all upper and lower teeth to come to full occlusion, the attachment of said dividing means to the respective U-shaped walls combined with the rigidity of the respective dividing means being sufficient to enable said dividing means to support impression material contained in the dental tray;

means adapted to maintain said upper tray section in position with respect to said lower tray section once they have been positionally adjusted with respect to each other;

a handle secured to the anterior portion of the U-shaped wall of at least the one tray section adapted to receive overbiting or underbiting teeth, whereby impressions of teeth having overbite or underbite characteristics are obtained without said handle interfering with proper registration; and a cavity formed in at least one tray section adjacent the anterior portion of the U-shaped peripheral retaining wall, said cavity extending below the plane of the dividing means of at least one tray section to accommodate a gross overbite or underbite condition.

* * * * *